United States Patent
Grammenos et al.

(10) Patent No.: US 7,388,018 B2
(45) Date of Patent: Jun. 17, 2008

(54) 4-PIRIDINYLMETHYLSULPHONAMIDE DERIVATIVES AS FUNGICIDAL PLANT PROTEIN AGENTS

(75) Inventors: Wassilios Grammenos, Ludwigshafen (DE); Carsten Blettner, Mannheim (DE); Bernd Müller, Frankenthal (DE); Markus Gewehr, Kastellaun (DE); Jordi Tormo i Blasco, Laudenbach (DE); Thomas Grote, Wachenheim (DE); Joachim Rheinheimer, Ludwigshafen (DE); Peter Schäfer, Ottersheim (DE); Frank Schieweck, Heβheim (DE); Anja Schwögler, Mannheim (DE); Oliver Wagner, Neustadt (DE); Norbert Götz, Worms (DE); Siegfried Strathmann, Limburgerhof (DE); Ulrich Schöfl, Brühl (DE); Maria Scherer, Godramstein (DE); Reinhard Stierl, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 122 days.

(21) Appl. No.: 10/570,893

(22) PCT Filed: Sep. 10, 2004

(86) PCT No.: PCT/EP2004/010124

§ 371 (c)(1),
(2), (4) Date: Mar. 7, 2006

(87) PCT Pub. No.: WO2005/033081

PCT Pub. Date: Apr. 14, 2005

(65) Prior Publication Data

US 2006/0293314 A1   Dec. 28, 2006

(30) Foreign Application Priority Data

Sep. 18, 2003 (EP) ................... 03021098

(51) Int. Cl.
*A61K 31/541* (2006.01)
*A61K 31/496* (2006.01)
*C07D 417/02* (2006.01)
*C07D 403/02* (2006.01)

(52) U.S. Cl. ............ 514/299; 514/311; 514/329; 514/341; 514/342; 546/112; 546/134; 546/256; 546/272.7; 546/275.4; 546/280.4; 546/329

(58) Field of Classification Search ........ 546/112, 546/134, 329; 514/299, 311, 357
See application file for complete search history.

(56) References Cited

U.S. PATENT DOCUMENTS 4,699,652 A   10/1987   Zehnder

FOREIGN PATENT DOCUMENTS

| EP | 0 206 581 A | 12/1986 |
|---|---|---|
| EP | 0 209 854 A | 1/1987 |
| EP | 1 174 028 A | 1/2002 |
| GB | 2 078 215 A | 1/1982 |
| WO | WO-00/06083 A2 | 2/2000 |

OTHER PUBLICATIONS

Miguel F. Brana et al., Liebigs Ann. Chem. 1990, 641-645.

*Primary Examiner*—Zinna N. Davis
(74) *Attorney, Agent, or Firm*—Birch, Stewart, Kolasch & Birch, LLP

(57) ABSTRACT

Sulfonamides of the formula I

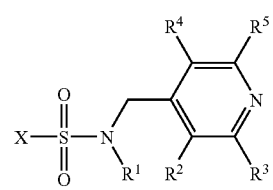

where the substituents are as follows:
$R^1$ is hydrogen, alkyl, alkoxy, alkenyl or alkynyl; and
$R^2$, $R^3$, $R^4$, $R^5$ are hydrogen, halogen, alkyl, alkoxy or halomethyl;
$R^2$ and $R^3$ together may also form a phenyl, cyclopentyl or cyclohexyl ring, it being possible for these rings to carry two groups $R^2$, and $R^3$,
$R^2$, $R^3$, are hydrogen, halogen, alkyl, alkoxy or halomethyl;
in case a), if $R^2$, $R^3$, $R^4$ and $R^5$ are hydrogen:
X is phenyl substituted by a group —$C(R^6)$=$NOR^7$, where
$R^6$ is alkyl and
$R^7$ is alkyl, benzyl, alkenyl, haloalkyl, haloalkenyl, alkynyl or haloalkynyl; and
in case b), if at least one of the groups $R^2$, $R^3$, $R^4$ and $R^5$ is not hydrogen:
X is phenyl, naphthyl or a five- or six-membered saturated, or partially unsaturated or aromatic heterocycle which is attached via a carbon atom and contains one to four heteroatoms from the group consisting of O, N and S, where X may be substituted according to the description;

Processes for preparing these compounds, compositions comprising them and their use for controlling phytopathogenic harmful fungi.

20 Claims, No Drawings

4-PIRIDINYLMETHYLSULPHONAMIDE DERIVATIVES AS FUNGICIDAL PLANT PROTEIN AGENTS

The present invention relates to sulfonamides of the formula I

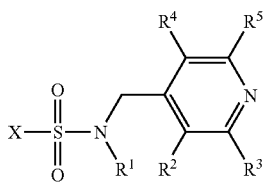

where the substituents are as follows:

$R^1$ is hydrogen, $C_1$-$C_4$-alkyl, $C_1$-$C_4$-alkoxy, $C_2$-$C_4$-alkenyl, $C_2$-$C_4$-alkynyl or benzyl;

$R^2$, $R^3$, $R^4$, $R^5$ independently of one another are hydrogen, halogen, $C_1$-$C_4$-alkyl, $C_1$-$C_4$-alkoxy or $C_1$-halomethyl;

$R^2$ and $R^3$ together may also form a phenyl, cyclopentyl or cyclohexyl ring, it being possible for these rings to carry two groups $R^2$, and $R^3$, , $R^2$, , $R^3$, independently of one another are hydrogen, halogen, $C_1$-$C_4$-alkyl, $C_1$-$C_4$-alkoxy or $C_1$-halomethyl;

in case a), if $R^2$, $R^3$, $R^4$ and $R^5$ are hydrogen:

X is phenyl substituted by a group —$C(R^6)$=$NOR^7$, where
  $R^6$ is $C_1$-$C_4$-alkyl and
  $R^7$ is $C_1$-$C_8$-alkyl, benzyl, $C_2$-$C_4$-alkenyl, $C_1$-$C_4$-haloalkyl, $C_2$-$C_4$-haloalkenyl, $C_2$-$C_4$-alkynyl or $C_2$-$C_4$-haloalkynyl; and in case b), if at least one of the groups $R^2$, $R^3$, $R^4$ and $R^5$ is not hydrogen:

X is phenyl, naphthyl or a five- or six-membered saturated, partially unsaturated or aromatic heterocycle which is attached via a carbon atom and contains one to four heteroatoms selected from the group consisting of O, N and S, where X may carry one to four groups $R^a$:

$R^a$ is halogen, cyano, nitro, $C_1$-$C_8$-alkyl, $C_1$-$C_8$-alkoxy, $C_1$-$C_8$-haloalkoxy, $C_1$-$C_4$-alkylcarbonyl, $C_1$-$C_4$-alkoxycarbonyl, —$C(R^6)$=$NOR^7$, $C_1$-$C_4$-alkylaminocarbonyl, di($C_1$-$C_4$-alkyl)aminocarbonyl or phenyl or phenoxy, where the rings may carry one to three groups $R^b$:

$R^b$ is halogen, $C_1$-$C_4$-alkyl, $C_1$-$C_4$-alkoxy, $C_1$-haloalkyl or $C_1$-haloalkoxy;

$R^a$ or $R^b$ may also be a $C_3$-$C_4$-alkylene or a $C_4$-alkenylene group which, together with two adjacent ring members of the phenyl ring to which it is attached, forms a ring which may be substituted by one or more of the abovementioned groups $R^a$ or $R^b$.

Moreover, the invention relates to processes for preparing these compounds, to compositions comprising them and to their use for controlling phytopathogenic harmful fungi.

In a general manner, DE-A 31 22 700 and WO 00/06083 disclose pyridinosulfonamides as pharmaceuticals. The general disclosure of these documents comprises 4-pyridinemethylsulfonamides.

Individual 4-pyridinemethylsulfonamides are known from EP-A 206 581 and Lieb. Ann. Chem. 641 (1990). The compounds described in the publications mentioned are suitable for controlling harmful fungi.

However, in many cases their action is unsatisfactory. Based on this, it is an object of the present invention to provide compounds having improved action and/or a broader activity spectrum.

Accordingly we have found that this object is achieved by the compounds defined at the outset. Furthermore, we have found processes and intermediates for their preparation, compositions comprising them and methods for controlling harmful fungi using the compounds I.

The compounds according to the invention differ from those described in EP-A 206 581, DE-A 31 22 700 and WO 00/06083 by the 4-pyridinomethyl group and from the compounds known from Lieb. Ann. Chem. 641 (1990) by the substitution of the pyridine ring or group X.

Compared to the known compounds, the compounds of the formula I have increased activity against harmful fungi.

The compounds according to the invention can be obtained by different routes. Advantageously, they are obtained from pyridine derivatives of the formula II by reaction with sulfonic acids or activated sulfonic acid derivatives of the formula III in which X is as defined in claim 1, under basic condtions. In formula III, L is hydroxyl or halogen, preferably chlorine.

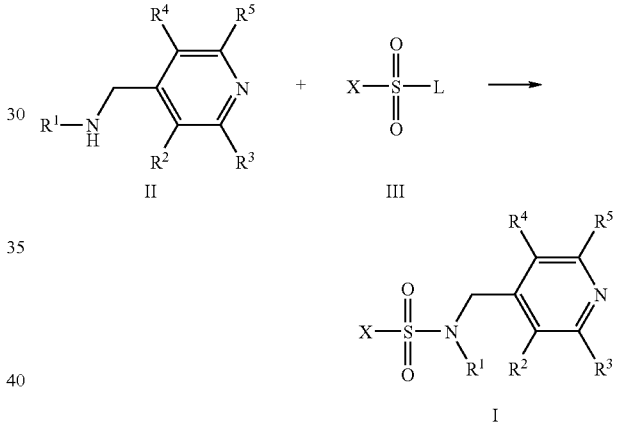

This reaction is usually carried out at temperatures from −30° C. to 120° C., preferably from −10° C. to 100° C., in an inert organic solvent in the presence of a base [cf. Lieb. Ann. Chem. 641 (1990)].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butylmethyl ether, dioxane, anisole and tetrahydrofuran, nitriles, such as acetonitrile and propionitrile, ketones, such as acetone, methylethyl ketone, diethyl ketone and tert-butyl methyl ketone, and also dimethyl sulfoxide, dimethylformamide and dimethylacetamide, particularly preferably diisopropyl ether, diethyl ether and tetrahydrofuran. It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide, and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, triisopropylethylamine and N-methylpiperidine, pyridine, substituted pyridines, such as collidine, lutidine and 4-dimethylaminopyridine, and also bicyclic amines. Particular preference is given to pyridine, triethylamine and potassium carbonate. The bases are generally employed in catalytic amounts; however, they can also be used in equimolar amounts, in excess or, if appropriate, as solvent.

The starting materials are generally reacted with one another in equimolar amounts. In terms of yield, it may be advantageous to employ an excess of II, based on III.

The starting materials required for preparing the compounds I are commercially available or known from the literature [J. für praktische Chemie, p. 695 (1994); Heterocycles, p. 675 (1995); Tetrahedron, p. 12483 (1996); Chem. Pharm. Bull., p. 1927 (1973); J. Chem. Soc., p. 426 (1942); EP-A 983 982; Synthesis, p. 852 (1986)] or can be prepared in accordance with the literature cited.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, purification can also be carried out by recrystallization or digestion.

If individual compounds I cannot be obtained by the routes described above, they can be prepared by derivatization of other compounds I.

However, if the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the harmful fungus to be controlled.

In the definitions of the symbols given in the formulae above, collective terms were used which are generally representative of the following substituents:

halogen: fluorine, chlorine, bromine and iodine;

alkyl: saturated straight-chain or branched hydrocarbon radicals having 1 to 4, 6 or 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 2 or 4 carbon atoms (as mentioned above), where in these groups some or all of the hydrogen atoms may be replaced by halogen atoms as mentioned above; in particular, $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl: unsaturated straight-chain or branched hydrocarbon radicals having 2 to 4, 6 or 8 carbon atoms and one or two double bonds in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

haloalkenyl: unsaturated straight-chain or branched hydrocarbon radicals having 2 to 6 carbon atoms and one or two double bonds in any position (as mentioned above), where in these groups some or all of the hydrogen atoms may be replaced by halogen atoms as mentioned above, in particular by fluorine, chlorine and bromine;

alkynyl: straight-chain or branched hydrocarbon groups having 2 to 4, 6 or 8 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: mono- or bicyclic saturated hydrocarbon groups having 3 to 6 or 8 carbon ring members, for example $C_3$-$C_8$-cycloalkyl such as cyclopropyl, cyclobutyl, cyclopentyl, cyclohexyl, cycloheptyl and cyclooctyl;

five- to ten-membered saturated, partially unsaturated or aromatic heterocycle which contains one to four heteroatoms from the group consisting of O, N and S:

- 5- or 6-membered heterocyclyl which contains one to three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl and 2-piperazinyl;
- 5-membered heteroaryl which contains one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example, 2-thienyl, 3-thienyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl and 1,3,4-triazol-2-yl;
- 6-membered heteroaryl which contains one to three or one to four nitrogen atoms: 6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl;

alkylene: divalent unbranched chains of 3 to 5 $CH_2$ groups, for example $CH_2$, $CH_2CH_2$, $CH_2CH_2CH_2$, $CH_2CH_2CH_2CH_2$ and $CH_2CH_2CH_2CH_2CH_2$;

oxyalkylene: divalent unbranched chains of 2 to 4 $CH_2$ groups, where one valency is attached to the skeleton via an oxygen atom, for example $OCH_2CH_2$, $OCH_2CH_2CH_2$ and $OCH_2CH_2CH_2CH_2$;

oxyalkyleneoxy: divalent unbranched chains of 1 to 3 $CH_2$ groups, where both valencies are attached to the skeleton via an oxygen atom, for example $OCH_2O$, $OCH_2CH_2O$ and $OCH_2CH_2CH_2O$;

Alkenylene: divalent unbranched chains of 4 or 6 CH groups which are linked by conjugated C=C double bonds, for example CH=CH or CH=CH—CH=CH.

The scope of the present invention includes the (R)- and (S)-isomers and the racemates of compounds of the formula I having chiral centers.

With a view to the intended use of the sulfonamides of the formula I, particular preference is given to the following meanings of the substituents, in each case on their own or in combination:

The invention preferably provides compounds of the formula I, in which $R^1$ is hydrogen, methyl, methoxy, ethoxy, allyl or propargyl, in particular hydrogen or methyl.

Preference is likewise given to compounds of the formula I, in which $R^2$, $R^3$, $R^4$ and $R^5$ independently of one another are hydrogen, methyl, ethyl, fluorine, chlorine, $CF_3$, $OCF_3$ or $OCHF_2$.

In addition, preference is also given to compounds of the formula I in which at least one, in particular one or two, groups selected from the group consisting of $R^2$, $R^3$, $R^4$ and $R^5$ are not hydrogen.

Preference is likewise also given to compounds of the formula I which are substituted by two identical groups selected from the group consisting of $R^2$, $R^3$, $R^4$ and $R^5$.

Further preferred embodiments of the formula I are in each case per se compounds of the formulae I.1 to I.6 where the variables are as defined for formula I:

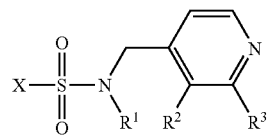

I.1

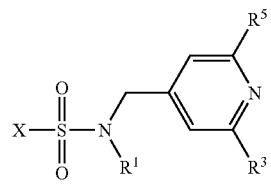

I.2

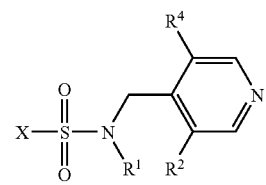

I.3

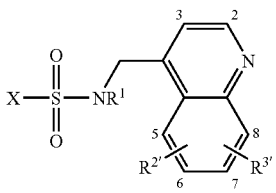

I.4

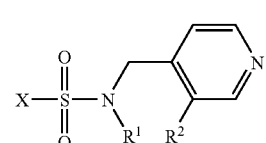

I.5

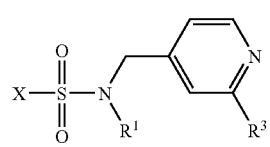

I.6

Preference is given to compounds of the formula I.4 in which the groups $R^{2'}$ and $R^{3'}$ are located in the 6,7-position.

Particular preference is given to compounds of the formula I in which X is a phenyl ring which carries a group $R^a$ in the para-position; these compounds correspond to the formula IA:

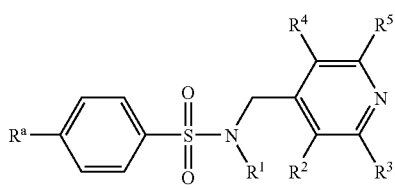

Particular preference is given to compounds of the formula I in which $R^a$ has the following meanings: $C(R^6)=NOR^7$, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, chloromethyl, dichloromethyl, trichloromethyl, fluoromethyl, di-fluoromethyl, trifluoromethyl, dichlorofluoromethyl, chlorodifluoromethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, trichloromethoxy, fluoro-methoxy, difluoromethoxy, trifluoromethoxy, chlorodifluoromethoxy, 2,2-difluoroethoxy, 2,2,2-trifluoroethoxy, 2,2,2-trichloroethoxy and pentafluoroethoxy.

A particularly preferred embodiment of $R^6$ is methyl; $R^7$ is preferably methyl, ethyl, allyl or propargyl, it being possible for the groups $R^7$ to be halogenated.

In particular with a view to their use, preference is given to the compounds I compiled in the tables below. Moreover, the groups mentioned for a substituent in the tables are per se, independently of the combination in which they are mentioned, a particularly preferred embodiment of the substituent in question.

Table 1
Compounds of the formula IA, in which $R^2$, $R^3$, $R^4$ and $R^5$ are hydrogen and the combination of $R^1$ and $R^a$ corresponds for each compound to one row A-1 to A-14 of Table A Table 2
Compounds of the formula IA.1, in which $R^2$ and $R^3$ are methyl and the combination of $R^1$ and $R^a$ corresponds for each compound to one row of Table A

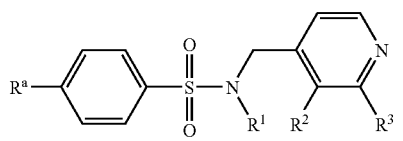

Table 3
Compounds of the formula IA.1, in which $R^2$ and $R^3$ are fluorine and the combination of $R^1$ and $R^a$ corresponds for each compound to one row of Table A Table 4
Compounds of the formula IA.1, in which $R^2$ and $R^3$ are chlorine and the combination of $R^1$ and $R^a$ corresponds for each compound to one row of Table A Table 5
Compounds of the formula IA.1, in which $R^2$ and $R^3$ are methoxy and the combination of $R^1$ and $R^a$ corresponds for each compound to one row of Table A Table 6
Compounds of the formula IA.1, in which $R^2$ and $R^3$ are trifluoromethoxy and the combination of $R^1$ and $R^a$ corresponds for each compound to one row of Table A Table 7
Compounds of the formula IA.2, in which $R^3$ and $R^5$ are methyl and the combination of $R^1$ and $R^a$ corresponds for each compound to one row of Table A

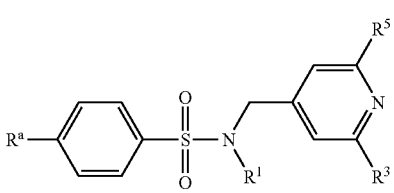

Table 8
Compounds of the formula IA.2, in which $R^3$ and $R^5$ are fluorine and the combination of $R^1$ and $R^a$ corresponds for each compound to one row of Table A Table 9
Compounds of the formula IA.2, in which $R^3$ and $R^5$ are chlorine and the combination of $R^1$ and $R^a$ corresponds for each compound to one row of Table A Table 10
Compounds of the formula IA.2, in which $R^3$ and $R^5$ are methoxy and the combination of $R^1$ and $R^a$ corresponds for each compound to one row of Table A Table 11
Compounds of the formula IA.2, in which $R^3$ and $R^5$ are trifluoromethoxy and the combination of $R^1$ and $R^a$ corresponds for each compound to one row of Table A Table 12
Compounds of the formula IA.3, in which $R^2$ and $R^4$ are methyl and the combination of $R^1$ and $R^a$ corresponds for each compound to one row of Table A

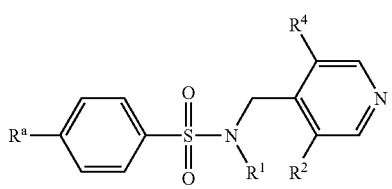

Table 13
Compounds of the formula IA.3, in which $R^2$ and $R^4$ are fluorine and the combination of $R^1$ and $R^a$ corresponds for each compound to one row of Table A Table 14
Compounds of the formula IA.3, in which $R^2$ and $R^4$ are chlorine and the combination of $R^1$ and $R^a$ corresponds for each compound to one row of Table A Table 15
Compounds of the formula IA.3, in which $R^2$ and $R^4$ are methoxy and the combination of $R^1$ and $R^a$ corresponds for each compound to one row of Table A Table 16
Compounds of the formula IA.3, in which $R^2$ and $R^4$ are trifluoromethoxy and the combination of $R^1$ and $R^a$ corresponds for each compound to one row of Table A Table 17
Compounds of the formula IA.4', in which $R^2$ and $R^3$ are hydrogen and the combination of $R^1$ and $R^a$ corresponds for each compound to one row of Table A

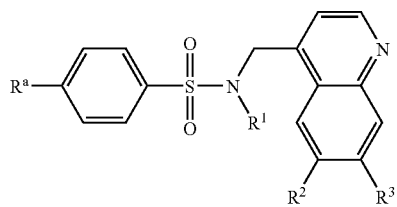

IA.4'

Table 18
Compounds of the formula IA.4', in which $R^2$ and $R^3$ are methyl and the combination of $R^1$ and $R^a$ corresponds for each compound to one row of Table A Table 19
Compounds of the formula IA.4', in which $R^2$ and $R^3$ are fluorine and the combination of $R^1$ and $R^a$ corresponds for each compound to one row of Table A Table 20
Compounds of the formula IA.4', in which $R^2$ and $R^3$ are chlorine and the combination of $R^1$ and $R^a$ corresponds for each compound to one row of Table A Table 21
Compounds of the formula IA.4', in which $R^2$ and $R^3$ are methoxy and the combination of $R^1$ and $R^a$ corresponds for each compound to one row of Table A Table 22
Compounds of the formula IA.4', in which $R^2$ and $R^3$ are trifluoromethoxy and the combination of $R^1$ and $R^a$ corresponds for each compound to one row of Table A Table 23
Compounds of the formula IA.5, in which $R^2$ is methyl and the combination of $R^1$ and $R^a$ corresponds for each compound to one row of Table A

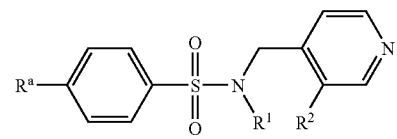

IA.5

Table 24
Compounds of the formula IA.5, in which $R^2$ is fluorine and the combination of $R^1$ and $R^a$ corresponds for each compound to one row of Table A Table 25
Compounds of the formula IA.5, in which $R^2$ is chlorine and the combination of $R^1$ and $R^a$ corresponds for each compound to one row of Table A Table 26
Compounds of the formula IA.5, in which $R^2$ is methoxy and the combination of $R^1$ and $R^a$ corresponds for each compound to one row of Table A Table 27
Compounds of the formula IA.5, in which $R^2$ is trifluoromethoxy and the combination of $R^1$ and $R^a$ corresponds for each compound to one row of Table A Table 28
Compounds of the formula IA.6, in which $R^3$ is methyl and the combination of $R^1$ and $R^a$ corresponds for each compound to one row of Table A

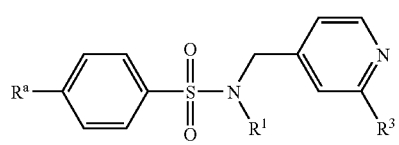

IA.6

Table 29
Compounds of the formula IA.6, in which $R^3$ is fluorine and the combination of $R^1$ and $R^a$ corresponds for each compound to one row of Table A Table 30
Compounds of the formula IA.6, in which $R^3$ is chlorine and the combination of $R^1$ and $R^a$ corresponds for each compound to one row of Table A Table 31
Compounds of the formula IA.6, in which $R^3$ is methoxy and the combination of $R^1$ and $R^a$ corresponds for each compound to one row of Table A Table 32
Compounds of the formula IA.6, in which $R^3$ is trifluoromethoxy and the combination of $R^1$ and $R^a$ corresponds for each compound to one row of Table A

TABLE A

| No. | $R^1$ | $R^a$ |
|---|---|---|
| A-1 | H | $C(CH_3)=NOCH_3$ |
| A-2 | $CH_3$ | $C(CH_3)=NOCH_3$ |
| A-3 | H | $C(CH_3)=NOCH_2CH_3$ |
| A-4 | $CH_3$ | $C(CH_3)=NOCH_2CH_3$ |
| A-5 | H | $C(CH_3)=NOCH_2CH=CH_2$ |
| A-6 | $CH_3$ | $C(CH_3)=NOCH_2CH=CH_2$ |
| A-7 | H | $C(CH_3)=NOCH_2C\equiv CH$ |
| A-8 | $CH_3$ | $C(CH_3)=NOCH_2C\equiv CH$ |
| A-9 | H | $C(CH_3)=NOCH_2CCl=CH_2$ |
| A-10 | $CH_3$ | $C(CH_3)=NOCH_2CCl=CH_2$ |
| A-11 | H | H |
| A-12 | $CH_3$ | H |
| A-13 | H | $CH_3$ |
| A-14 | $CH_3$ | $CH_3$ |
| A-15 | H | $CH_2CH_3$ |
| A-16 | $CH_3$ | $CH_2CH_3$ |
| A-17 | H | $CH_2CH_2CH_3$ |
| A-18 | $CH_3$ | $CH_2CH_2CH_3$ |
| A-19 | H | $CH(CH_3)_2$ |
| A-20 | $CH_3$ | $CH(CH_3)_2$ |
| A-21 | H | $CH_2CH_2CH_2CH_3$ |
| A-22 | $CH_3$ | $CH_2CH_2CH_2CH_3$ |
| A-23 | H | $CH(CH_3)CH_2CH_3$ |
| A-24 | $CH_3$ | $CH(CH_3)CH_2CH_3$ |
| A-25 | H | $CH_2CH(CH_3)_2$ |
| A-26 | $CH_3$ | $CH_2CH(CH_3)_2$ |

TABLE A-continued

| No. | R¹ | Rᵃ |
|---|---|---|
| A-27 | H | C(CH$_3$)$_3$ |
| A-28 | CH$_3$ | C(CH$_3$)$_3$ |
| A-29 | H | OCH$_3$ |
| A-30 | CH$_3$ | OCH$_3$ |
| A-31 | H | OCH$_2$CH$_3$ |
| A-32 | CH$_3$ | OCH$_2$CH$_3$ |
| A-33 | H | OCH$_2$CH$_2$CH$_3$ |
| A-34 | CH$_3$ | OCH$_2$CH$_2$CH$_3$ |
| A-35 | H | OCH(CH$_3$)$_2$ |
| A-36 | CH$_3$ | OCH(CH$_3$)$_2$ |
| A-37 | H | OCH$_2$CH$_2$CH$_2$CH$_3$ |
| A-38 | CH$_3$ | OCH$_2$CH$_2$CH$_2$CH$_3$ |
| A-39 | H | OCH(CH$_3$)CH$_2$CH$_3$ |
| A-40 | CH$_3$ | OCH(CH$_3$)CH$_2$CH$_3$ |
| A-41 | H | OCH$_2$CH(CH$_3$)$_2$ |
| A-42 | CH$_3$ | OCH$_2$CH(CH$_3$)$_2$ |
| A-43 | H | OC(CH$_3$)$_3$ |
| A-44 | CH$_3$ | OC(CH$_3$)$_3$ |
| A-45 | H | CCl$_3$ |
| A-46 | CH$_3$ | CCl$_3$ |
| A-47 | H | CHF$_2$ |
| A-48 | CH$_3$ | CHF$_2$ |
| A-49 | H | CF$_3$ |
| A-50 | CH$_3$ | CF$_3$ |
| A-51 | H | CHClF |
| A-52 | CH$_3$ | CHClF |
| A-53 | H | CH$_2$CHF$_2$ |
| A-54 | CH$_3$ | CH$_2$CHF$_2$ |
| A-55 | H | CH$_2$CF$_3$ |
| A-56 | CH$_3$ | CH$_2$CF$_3$ |
| A-57 | H | CF$_2$CF$_3$ |
| A-58 | CH$_3$ | CF$_2$CF$_3$ |
| A-59 | H | OCHCl$_2$ |
| A-60 | CH$_3$ | OCHCl$_2$ |
| A-61 | H | OCCl$_3$ |
| A-62 | CH$_3$ | OCCl$_3$ |
| A-63 | H | OCH$_2$F |
| A-64 | CH$_3$ | OCH$_2$F |
| A-65 | H | OCHF$_2$ |
| A-66 | CH$_3$ | OCHF$_2$ |
| A-67 | H | OCF$_3$ |
| A-68 | CH$_3$ | OCF$_3$ |
| A-69 | H | OCH$_2$CHF$_2$ |
| A-70 | CH$_3$ | OCH$_2$CHF$_2$ |
| A-71 | H | OCH$_2$CF$_3$ |
| A-72 | CH$_3$ | OCH$_2$CF$_3$ |
| A-73 | H | OCH$_2$CHClF |
| A-74 | CH$_3$ | OCH$_2$CHClF |
| A-75 | H | OCH$_2$CCl$_3$ |
| A-76 | CH$_3$ | OCH$_2$CCl$_3$ |
| A-77 | H | OCF$_2$CF$_3$ |
| A-78 | CH$_3$ | OCF$_2$CF$_3$ |
| A-79 | H | C$_6$H$_5$ |
| A-80 | CH$_3$ | C$_6$H$_5$ |
| A-81 | H | OC$_6$H$_5$ |
| A-82 | CH$_3$ | OC$_6$H$_5$ |

The compounds I are suitable as fungicides. They are distinguished by an outstanding effectiveness against a broad spectrum of phytopathogenic fungi, especially from the classes of the *Ascomycetes, Deuteromycetes, Oomycetes* and *Basidiomycetes*. Some are systemically effective and can be used in plant protection as foliar and soil fungicides.

They are particularly important in the control of a multitude of fungi on various cultivated plants, such as wheat, rye, barley, oats, rice, maize, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on fruit and vegetables,
*Bipolaris* and *Drechslera* species on cereals, rice and lawns,
*Blumeria graminis* (powdery mildew) on cereals,
*Botrytis cinerea* (gray mold) on strawberries, vegetables, ornamental plants and grapevines,
*Erysiphe cichoracearum* and *Sphaerotheca fuliginea* on cucurbits,
*Fusarium* and *Verticillium* species on various plants,
*Mycosphaerella* species on cereals, bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria tritici* and *Stagonospora nodorum* on wheat,
*Uncinula necator* on grapevines,
*Ustilago* species on cereals and sugar cane, and
*Venturia* species (scab) on apples and pears.

The compounds I are also suitable for controlling harmful fungi, such as *Paecilomyces variotii*, in the protection of materials (e.g. wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 1 g, preferably 0.01 to 0.05 g, per kilogram of seed are generally required.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted into the customary formulations, for example solutions, emulsions, suspensions, dusts, powders, pastes and granules. The application form depends on the particular purpose; in each case, it should ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutyinaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone or water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise between 0.01 and 95% by weight, preferably between 0.1 and 90% by weight, of the active compound. The active compounds are employed in a purity of from 90% to 100%, preferably 95% to 100% (according to NMR spectrum).

The Following are Examples of Formulations: 1. Products for Dilution with Water

A Water-soluble Concentrates (SL)

10 parts by weight of a compound according to the invention are dissolved in water or in a water-soluble solvent. As an alternative, wetters or other auxiliaries are added. The active compound dissolves upon dilution with water.

B Dispersible Concentrates (DC)

20 parts by weight of a compound according to the invention are dissolved in cyclohexanone with addition of a dispersant, for example polyvinylpyrrolidone. Dilution with water gives a dispersion.

C Emulsifiable Concentrates (EC)

15 parts by weight of a compound according to the invention are dissolved in xylene with addition of calcium dodecylbenzenesulfonate and castor oil ethoxylate (in each case 5%). Dilution with water gives an emulsion.

D Emulsions (EW, EO)

40 parts by weight of a compound according to the invention are dissolved in xylene with addition of calcium dodecylbenzenesulfonate and castor oil ethoxylate (in each case 5%). This mixture is introduced into water by means of an emulsifying machine (Ultraturrax) and made into a homogeneous emulsion. Dilution with water gives an emulsion.

E Suspensions (SC, OD)

In an agitated ball mill, 20 parts by weight of a compound according to the invention are comminuted with addition of dispersants, wetters and water or an organic solvent to give a fine active compound suspension. Dilution with water gives a stable suspension of the active compound.

F Water-dispersible Granules and Water-soluble Granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active compound.

G Water-dispersible Powders and Water-soluble Powders (WP, SP)

75 parts by weight of a compound according to the invention are ground in a rotor-stator mill with addition of dispersants, wetters and silica gel. Dilution with water gives a stable dispersion or solution of the active compound.

2. Products to be Applied Undiluted

H Dustable Powders (DP)

5 parts by weight of a compound according to the invention are ground finely and mixed intimately with 95% of finely divided kaolin. This gives a dustable product.

I Granules (GR, FG, GG, MG)

0.5 part by weight of a compound according to the invention is ground finely and associated with 95.5% carriers. Current methods are extrusion, spray-drying or the fluidized bed. This gives granules to be applied undiluted.

J ULV Solutions (UL)

10 parts by weight of a compound according to the invention are dissolved in an organic solvent, for example xylene. This gives a product to be applied undiluted.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; the intention is to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are between 0.0001 and 10%, preferably between 0.01 and 1%.

The active compounds may also be used successfully in the ultra-low-volume process (ULV), by which it is possible to apply formulations comprising over 95% by weight of active compound, or even to apply the active compound without additives.

Various types of oils, wetters, adjuvants, herbicides, fungicides, other pesticides, or bactericides may be added to the active compounds, if appropriate not until immediately prior to use (tank mix). These agents can be admixed with the agents according to the invention in a weight ratio of 1:10 to 10:1.

The compositions according to the invention can, in the use form as fungicides, also be present together with other active compounds, e.g. with herbicides, insecticides, growth regulators, fungicides or else with fertilizers. Mixing the compounds I or the compositions comprising them in the use form as fungicides with other fungicides results in many cases in an expansion of the fungicidal spectrum of activity being obtained.

The following list of fungicides, in conjunction with which the compounds according to the invention can be used, is intended to illustrate the possible combinations but does not limit them:

- acylalanines, such as benalaxyl, metalaxyl, ofurace or oxadixyl,
- amine derivatives, such as aldimorph, dodine, dodemorph, fenpropimorph, fenpropidin, guazatine, iminoctadine, spiroxamine or tridemorph,
- anilinopyrimidines, such as pyrimethanil, mepanipyrim or cyprodinyl,
- antibiotics, such as cycloheximide, griseofulvin, kasugamycin, natamycin, polyoxin or streptomycin,
- azoles, such as bitertanol, bromoconazole, cyproconazole, difenoconazole, dinitroconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole or triticonazole,
- dicarboximides, such as iprodione, myclozolin, procymidone or vinclozolin,
- dithiocarbamates, such as ferbam, nabam, maneb, mancozeb, metam, metiram, propineb, polycarbamate, thiram, ziram or zineb,
- heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine,
- copper fungicides, such as Bordeaux mixture, copper acetate, copper oxychloride or basic copper sulfate,
- nitrophenyl derivatives, such as binapacryl, dinocap, dinobuton or nitrophthalisopropyl,
- phenylpyrroles, such as fenpiclonil or fludioxonil,
- sulfur,
- other fungicides, such as acibenzolar-S-methyl, benthiavalicarb, carpropamid, chlorothalonil, cyflufenamid, cymoxanil, dazomet, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene or zoxamide,
- strobilurins, such as azoxystrobin, dimoxystrobin, fluoxastrobin, kresoxim-methyl, metominostrobin, orysastrobin, picoxystrobin, pyraclostrobin or trifloxystrobin,
- sulfenic acid derivatives, such as captafol, captan, dichlofluanid, folpet or tolylfluanid,
- cinnamides and analogous compounds, such as dimethomorph, flumetover or flumorph.

SYNTHESIS EXAMPLES

The procedures described in the synthesis examples below were used to prepare further compounds I by appropriate modification of the starting compounds. The compounds thus obtained are listed in the tables below, together with physical data.

Example 1

Preparation of 4-acetyl-N-pyridin-4-ylmethylphenylsulfonamide

At −10° C., a solution of 4.95 g (45.7 mmol) of 4-(aminomethyl)pyridine (4-picolylamine) in 10 ml of diethyl ether was added dropwise to a solution of 10 g (45.7 mmol) of 4-acetylsulfonyl chloride in 150 ml of diethyl ether, and the solution was then stirred at 20-25° C. for about 18 hours. The product was filtered off with suction and the residue was washed with dilute $NaHCO_3$ solution and water and then dried. This gave 5.2 g of the title compound of m.p.: 162-167° C.

Example 2

Preparation of 4-(1-ethoxyiminoethyl)-N-pyridin-4-ylmethylphenylsulfonamide 0.42 g of a 40% strength aqueous O-ethylhydroxylamine solution was added to a solution of 0.4 g (1.3 mmol) of the compound from Example 1 in 20 ml of methanol. Using 10% strength hydrochloric acid, the mixture was acidified to pH 4, and the solution was then stirred at 20-25° C. for about 18 hours. The reaction solution was poured into water and adjusted to pH 8 using $NaHCO_3$. The mixture was then extracted with methyl tert-butyl ether (MtBE), and the combined organic phases were washed with water and dried. Removal of the solvent gave 0.4 g of the title compound as a viscous oil.

$^1$H-NMR (δ, $CDCl_3$, ): 8.5 (d, 2H); 7.5 (m, 4H); 7.1 (d, 2H); 5.0 (t, 1H); 4.25 (q, 2H); 4.1 (d, 2H); 2.25 (s, 3H); 1.3 (t, 3H).

Example 3

Preparation of 4-(1-ethoxyimino-ethyl)-N-methyl-N-pyridin-4-ylmethylphenylsulfonamide

0.4 g (1.2 mmol) of the compound from Example 2 was added to a slurry of 0.04 g (1.32 mmol) of NaH (95% pure) in 50 ml of dimethylformamide (DMF), and the mixture was then stirred at 20-25° C. for 10 min. A solution of 0.17 g (1.2 mmol) of iodomethane in 10 ml of DMF was then added dropwise, and the combined reaction solution was stirred at 20-25° C. for about 18 hours, poured into water and then extracted with MtBE. The the organic phases were washed with water and then dried. Removal of the solvent gave 0.3 g of the title compound as a viscous oil.

$^1$H-NMR (δ, CDCl$_3$, ): 8.6 (d, 2H); 7.8 (m, 4H); 7.25 (d, 2H); 4.25 (q, 2H); 4.1 (d, 2H); 2.6 (s, 3H); 2.25 (s, 3H); 1.25 (t, 3H).

TABLE I

I

| No. | X | R$^1$ | R$^2$ | R$^3$ | R$^4$ | R$^5$ | phys. data (mp.[° C.]; $^1$H-NMR δ [ppm]; MS m/e [M + H$^+$]) |
|---|---|---|---|---|---|---|---|
| I-1 | 4-(C[CH$_3$]=NOCH$_3$)—C$_6$H$_4$ | H | H | H | H | H | 4.2 (2H); 4.0 (3H); 2.25 (3H) |
| I-2 | 4-(C[CH$_3$]=NOCH$_2$CH$_3$)—C$_6$H$_4$ | H | H | H | H | H | 4.25 (2H); 4.2 (2H); 2.25 (3H); 1.3 (3H) |
| I-3 | 4-(C[CH$_3$]=NOCH$_2$CH=CH$_2$)—C$_6$H$_4$ | H | H | H | H | H | 5.2 (2H); 4.7 (2H); 4.05 (2H); 2.25 (3H) |
| I-4 | 4-(C[CH$_3$]=NOCH(CH$_3$)$_2$)—C$_6$H$_4$ | H | H | H | H | H | 4.45 (1H); 4.2 (2H); 2.25 (3H); 1.3 (6H) |
| I-5 | 4-(C[CH$_3$]=NOCH$_2$C≡CH)—C$_6$H$_4$ | H | H | H | H | H | 4.8 (2H); 4.2 (2H); 2.5 (1H); 2.3 (3H) |
| I-6 | 4-(C[CH$_3$]=NO(CH$_2$)$_5$CH$_3$)—C$_6$H$_4$ | H | H | H | H | H | 4.2 (2H); 4.1 (2H); 2.25 (3H); 0.9 (3H) |
| I-7 | 4-(C[CH$_3$]=NOCH$_2$C$_6$H$_5$)—C$_6$H$_4$ | H | H | H | H | H | 5.3 (2H); 4.25 (2H); 2.25 (3H) |
| I-8 | 4-(C[CH$_3$]=NOCH$_3$)—C$_6$H$_4$ | CH$_3$ | H | H | H | H | 4.2 (2H); 4.05 (3H); 2.65 (3H); 2.25 (3H) |
| I-9 | 4-(C[CH$_3$]=NOCH$_2$CH$_3$)—C$_6$H$_4$ | CH$_3$ | H | H | H | H | 4.25 (2H); 4.2 (2H); 2.7 (3H); 1.35 (3H) |
| I-10 | 4-(C[CH$_3$]NOCH$_2$CH$_3$)—C$_6$H$_4$ | CH$_2$CH$_3$ | H | H | H | H | 4.3 (2H); 4.2 (2H); 4.3 (2H); 4.2 (2H); 3.2 (2H); 2.2 (3H); 1.3 (3H); 0.9 (3H) |
| I-11 | 4-(C[CH$_3$]=NOCH$_2$CH$_3$)—C$_6$H$_4$ | CH$_2$C≡CH | H | H | H | H | 4.35 (2H); 4.25 (2H); 4.0 (2H); 2.25 (1H) |
| I-12 | 4-(C[CH$_3$]=NOCH$_2$CH$_3$)—C$_6$H$_4$ | C$_6$H$_5$CH$_2$ | H | H | H | H | 4.3 (2H); 4.25 (2H); 4.2 (2H); 2.25 (3H) |
| I-13 | 4-(C[CH$_3$]=NOCH$_2$CH$_3$)—C$_6$H$_4$ | CH$_2$CH=CH$_2$ | H | H | H | H | 5.5 (1H); 5.0 (2H); 4.3 (2H); 3.75 (2H) |
| I-14 | 4-COOCH$_3$—C$_6$H$_4$ | H | —CH=CH—CH=CH— | | H | H | 8.45 (1H); 8.0 (1H); 7.4 (1H); 4.5 (2H) |
| I-15 | 4-CH$_3$—C$_6$H$_4$ | H | —CH=CH—CHCH— | | H | H | 8.1 (1H); 7.3 (1H); 4.65 (2H); 1.3 (9H) |
| I-16 | 4-OCH$_3$—C$_6$H$_4$ | H | —CH=CH—CH=CH— | | H | H | 8.1 (1H); 4.6 (1H); 3.0 (1H); 1.3 (6H) |
| I-17 | 4-Cl—C$_6$H$_4$ | H | —CH=CH—CH=CH— | | H | H | m/e 333 |
| I-18 | 2,5-Cl$_2$—C$_6$H$_3$ | H | —CH=CH—CH=CH— | | H | H | m/e 367 |
| I-19 | 1-naphthyl | H | —CH=CH—CH=CH— | | H | H | m/e 349 |
| I-20 | 2-CH$_3$-6-CF$_3$—C$_6$H$_3$ | H | —CH=CH—CH=CH— | | H | H | m/e 381 |
| I-21 | 2-Cl-5-OCH$_3$—C$_6$H$_3$ | H | —CH=CH—CH=CH— | | H | H | m/e 363 |
| I-22 | 2,4-Cl$_2$—C$_6$H$_3$ | H | —CH=CH—CH=CH— | | H | H | m/e 367 |
| I-23 | 4-CN—C$_6$H$_4$ | H | —CH=CH—CH=CH— | | H | H | m/e 324 |
| I-24 | 2,6-Cl$_2$—C$_6$H$_3$ | H | —CH=CH—CH=CH— | | H | H | m/e 367 |
| I-25 | 2-Br—C$_6$H$_4$ | H | —CH=CH—CH=CH— | | H | H | m/e 379 |
| I-26 | 2,3-Cl$_2$—C$_6$H$_3$ | H | —CH=CH—CH=CH— | | H | H | m/e 367 |
| I-27 | 3,4-(OCH$_3$)$_2$—C$_6$H$_3$ | H | —CH=CH—CH=CH— | | H | H | m/e 358 |
| I-28 | 2-CH$_3$-6-Cl—C$_6$H$_3$ | H | —CH=CH—CH=CH— | | H | H | m/e 347 |
| I-29 | 2-Cl—C$_6$H$_4$ | H | —CH=CH—CH=CH— | | H | H | m/e 333 |
| I-30 | C$_6$H$_5$ | H | —CH=CH—CH=CH— | | H | H | 8.45 (1H); 8.0 (1H); 7.4 (1H); 4.5 (2H) |
| I-31 | 4-C(CH$_3$)$_3$—C$_6$H$_4$ | H | —CH=CH—CH=CH— | | H | H | 8.1 (1H); 7.3 (1H); 4.65 (2H); 1.3 (9H) 8.1 (1H); 4.6 (1H); |

TABLE I-continued

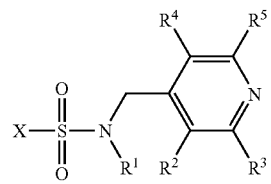

| No. | X | R¹ | R² | R³ | R⁴ | R⁵ | phys. data (mp.[° C.]; $^1$H-NMR δ [ppm]; MS m/e [M + H$^+$]) |
|---|---|---|---|---|---|---|---|
| I-32 | 4-CH(CH$_3$)$_2$—C$_6$H$_4$ | H | —CH=CH—CH=CH— | | H | H | 8.1 (1H); 4.6 (1H); 3.0 (1H); 1.3 (6H) |
| I-33 | 4-OCF$_3$—C$_6$H$_4$ | H | —CH=CH—CH=CH— | | H | H | 8.75 (1H); 8.0 (1H); 5.8 (1H); 4.7 (2H) |
| I-34 | 4-OCF$_2$CHF$_2$—C$_6$H$_4$ | H | —CH=CH—CH=CH— | | H | H | 8.8 (1H); 4.7 (2H) |
| I-35 | 4-COCH$_3$—C$_6$H$_4$ | H | —CH=CH—CH=CH— | | H | H | 8.8 (1H); 7.3 (1H); 4.6 (2H); 2.6 (3H) |
| I-36 | 4-(C[CH$_3$]=NOCH$_3$)—C$_6$H$_4$ | H | —CH=CH—CH=CH— | | H | H | 5.2 (NH); 4.6 (2H); 4.0 (3H); 2.2 (3H) |
| I-37 | 4-(C[CH$_3$]=NOCH$_2$CH$_3$)—C$_6$H$_4$ | H | —CH=CH—CH=CH— | | H | H | 5.0 (NH); 4.6 (2H); 4.3 (3H); 2.3 (3H); 1.35 (3H) |
| I-38 | 4-(C[CH$_3$]=NOCH(CH$_3$)$_2$)—C$_6$H$_4$ | H | —CH=CH—CH=CH— | | H | H | 5.1 (NH); 4.6 (2H); 4.5 5.1 (NH); 4.6 (2H); 4.5 (3H); 2.25 (3H); 1.3 (6H) |
| I-39 | 4-(C[CH$_3$]=NOCH$_2$CH=CH$_2$)—C$_6$H$_4$ | H | —CH=CH—CH=CH— | | H | H | 5.3 (NH); 5.2 (2H); 4.75 (2H); 4.6 (2H); 2.35 (3H) |
| I-40 | 4-(C[CH$_3$]=NOCH$_2$C≡CH)—C$_6$H$_4$ | H | —CH=CH—CH=CH— | | H | H | 5.1 (NH); 4.8 (2H); 4.6 (2H); 2.5 (2H); 2.3 (3H) |
| I-41 | 4-(C[CH$_3$]=NO(CH$_2$)$_5$CH$_3$)—C$_6$H$_4$ | H | —CH=CH—CH=CH— | | H | H | 5.2 (NH); 4.6 (2H); 4.2 (2H); 2.25 (2H); 0.9 (3H) |
| I-42 | 4-(C[CH$_3$]=NOCH$_2$C$_6$H$_5$)—C$_6$H$_4$ | H | —CH=CH—CH=CH— | | H | H | 5.3 (2H); 5.2 (NH); 4.8 (2H); 2.3 (3H) |
| I-43 | C$_6$H$_5$ | CH$_3$ | —CH=CH—CH=CH— | | H | H | 4.6 (2H); 2.7 (3H) |
| I-44 | 5-Cl-thiophen-2-yl | H | H | H | H | H | m/e 339 |
| I-45 | thiophen-2-yl | H | H | H | H | H | m/e 305 |
| I-46 | 5-([4-C(CH$_3$)$_3$]—C$_6$H$_4$)-thiophen-2-yl | H | H | H | H | H | 166 |
| I-47 | 5-Br-thiophen-2-yl | H | H | H | H | H | 148 |
| I-48 | 4-NO$_2$-5-Cl-thiophen-2-yl | H | H | H | H | H | 182 |
| I-49 | 5-Cl-1,3-(CH$_3$)$_2$-1H-pyrazol-4-yl | H | H | H | H | H | 147 |
| I-50 | 3-Br-2,5-Cl$_2$-thiophen-4-yl | H | H | H | H | H | 106 |
| I-51 | 1-CH$_3$-1H-imidazol-4-yl | H | H | H | H | H | 125 |
| I-52 | 5-(4-tert-butylphenyl)thiophen-2-yl | H | H | H | H | H | 166 |
| I-53 | 5-chloro-1,3-dimethyl-1H-pyrazol-4-yl | H | H | H | H | H | 147 |
| I-54 | 5-bromothiophen-2-yl | H | H | H | H | H | 148 |
| I-55 | 5-chloro-4-nitrothiophen-2-yl | H | H | H | H | H | 182 |
| I-56 | 1-methyl-1H-imidazol-4-yl | H | H | H | H | H | 125 |
| I-57 | 4-bromo-2,5-dichlorothiophen-3-yl | H | H | H | H | H | 106 |
| I-58 | 5-biphenyl-4-ylthiophen-2-yl | H | H | H | H | H | 204 |
| I-59 | 5-(4-trifluoromethoxyphenyl)thiophen-2-yl | H | H | H | H | H | 138 |
| I-60 | 5-(4-propylphenyl)thiophen-2-yl | H | H | H | H | H | 144 |
| I-61 | 5-(4-ethylphenyl)thiophen-2-yl | H | H | H | H | H | 144 |
| I-62 | 5-(3-trifluoromethylphenyl)thiophen-yl | H | H | H | H | H | 130 |
| I-63 | 5-(4-chlorophenyl)thiophen-2-yl | H | H | H | H | H | 176 |
| I-64 | 5-(4-trifluoromethylphenyl)thiophenyl | H | H | H | H | H | 165 |
| I-65 | 5-(4-methoxyphenyl)thiophen-2-yl | H | H | H | H | H | 175 |
| I-66 | 5-(4-trifluoromethylphenyl)thiophen-2-yl | propargyl | H | H | H | H | 116 |
| I-67 | 5-(4-trifluoromethylphenyl)thiophen-2-yl | n-propyl | H | H | H | H | 97 |
| I-68 | 5-(4-trifluoromethylphenyl)thiophen-2-yl | methyl | H | H | H | H | 101 |
| I-69 | 5-(4-isopropylphenyl)thiophen-2-yl | H | H | H | H | H | 125 |
| I-70 | 5-bromothiophen-2-yl | H | —CH=CH—CH=CH— | | H | H | 137 |
| I-71 | 5-(4-trifluoromethylphenyl)thiophen-2-yl | H | —CH=CH—CH=CH— | | H | H | 180 |
| I-72 | 4-tert-butylphenyl | methyl | —CH=CH—CH=CH— | | H | H | 145-148 |

Examples of the Activity Against Harmful Fungi

The fungicidal action of the compounds of the formula I was demonstrated by the following experiments:

The active compounds were prepared separately or together as a stock solution using 0.25% by weight of active compound in acetone or DMSO. 1% by weight of the emulsifier Uniperol® EL (wetting agent having emulsifying and dispersing action based on ethoxylated alkylphenols) was added to this solution, and the mixture was diluted with water to the desired concentration.

Use Example 1

Activity Against Early Blight of Tomatoes Caused by *Alternaria solani*

Leaves of potted plants of the cultivar "Goldene Prinzessin" were sprayed to runoff point with an aqueous suspension having the concentration of active compounds stated below. The next day, the leaves were infected with an aqueous spore suspension of *Alternaria solani* in a 2% biomalt solution having a density of $0.17 \times 10^6$ spores/ml. The plants were then placed in a water-vapor-saturated chamber at 20-22° C. After 5 days, the early blight on the untreated, but infected control plants had developed to such an extent that the infection could be determined visually in %.

In this test, the plants which had been treated with 250 ppm of active compounds I-2 to I-6, I-14, I-15, I-17, I-30 to I-34, I-36 to I-42 or I-45 had no more than 30% infection, whereas the untreated plants were 100% infected.

Use Example 2

Activity Against Mildew on Cucumber Leaves Caused by *Sphaerotheca fuliginea*, Protective Application Leaves of potted cucumber seedlings of the cultivar "Chinese Snake" were, at the cotyledon stage, sprayed to runoff point with an aqueous suspension having the concentration of active compounds stated below. 20 hours after the spray coating had dried on, the plants were inoculated with an aqueous spore suspension of mildew of cucumber (*Sphaerotheca fuliginea*). The plants were then cultivated in a greenhouse at 20-24° C. and 60-80% relative atmospheric humidity for 7 days. The extent of the mildew development was then determined visually in % infection of the cotyledon area.

In this test, the plants which had been treated with 250 ppm of the active compounds I-1 to I-5, I-15, I-18, I-30, I-32, I-33, I-34, I-37 to I-40, I-42 or I-45 showed no more than 30% infection, whereas the untreated plants were 100% infected.

We claim:
1. A sulfonamide of the formula I

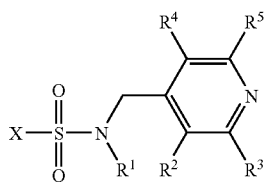

wherein:
$R^1$ is hydrogen, $C_1$-$C_4$-alkyl, $C_1$-$C_4$-alkoxy, $C_2$-$C_4$-alkenyl, $C_2$-$C_4$-alkynyl or benzyl;
$R^2$, $R^3$, $R^4$, and $R^5$ are independently of one another hydrogen, halogen, $C_1$-$C_4$-alkyl, $C_1$-$C_4$-alkoxy or halomethyl;

$R^2$ and $R^3$ together may also form a phenyl, cyclopentyl or cyclohexyl ring, it being possible for these rings to carry two groups $R^2$ and $R^3$,
$R^2$ and $R^3$ independently of one another are hydrogen, halogen, $C_1$-$C_4$-alkyl, $C_1$-$C_4$-alkoxy or halomethyl;
in case a), if $R^2$, $R^3$, $R^4$ and $R^5$ are hydrogen:
X is phenyl substituted by a group —$C(R^6)$=$NOR^7$, wherein
$R^6$ is $C_1$-$C_4$-alkyl and
$R^7$ is $C_1$-$C_8$-alkyl, benzyl, $C_2$-$C_4$-alkenyl, $C_1$-$C_4$-haloalkyl, $C_2$-$C_4$-haloalkenyl, $C_2$-$C_4$-alkynyl or $C_2$-$C_4$-haloalkynyl; and
in case b), if at least one of the groups $R^2$, $R^3$, $R^4$ and $R^5$ is not hydrogen:
X is phenyl, naphthyl or a five- or six-membered saturated, partially unsaturated or aromatic heterocycle which is attached via a carbon atom and contains one to four heteroatoms selected from the group consisting of O, N and S, where X may carry one to four groups $R^a$:
$R^a$ is halogen, cyano, nitro, $C_1$-$C_8$-alkyl, $C_1$-$C_8$-alkoxy, $C_1$-$C_8$-haloalkoxy, $C_1$-$C_4$-alkylcarbonyl, $C_1$-$C_4$-alkoxycarbonyl, —$C(R^6)$=$NOR^7$,
$C_1$-$C_4$-alkylaminocarbonyl, di($C_1$-$C_4$-alkyl)aminocarbonyl or phenyl or phenoxy, where the rings may carry one to three groups $R^b$:
$R^b$ is halogen, $C_1$-$C_4$-alkyl, $C_1$-$C_4$-alkoxy, $C_1$-$C_4$-haloalkyl or $C_1$-$C_8$-haloalkoxy;
$R^a$ or $R^b$ may also be a $C_3$-$C_4$-alkylene or a $C_4$-alkenylene group which, together with two adjacent ring members of the phenyl ring to which it is attached, forms a ring which may be substituted by one or more of the abovementioned groups $R^a$ or $R^b$.

2. The compound according to claim 1, wherein $R^2$, $R^3$, $R^4$ and $R^5$ independently of one another are hydrogen, methyl, fluorine, chlorine, $CF_3$, $OCF_3$ or $OCHF_2$.

3. The compound according to claim 1, wherein $R^1$ is hydrogen, methyl, methoxy, ethoxy, allyl or propargyl.

4. The compound according to claim 1, wherein X is a phenyl ring which is substituted in the para position.

5. The compound according to claim 1, wherein X is an aromatic heterocycle.

6. The compound according to claim 1, wherein X is a 2-thienyl or 3-thienyl.

7. The compound according to claim 1, wherein X is a 4-pyrazolyl.

8. The compound according to claim 1, wherein X is a 4-imidazolyl.

9. The compound according to claim 2, wherein $R^1$ is hydrogen, methyl, methoxy, ethoxy, allyl or propargyl.

10. The compound according to claim 2, wherein X is a phenyl ring which is substituted in the para position.

11. The compound according to claim 3, wherein X is a phenyl ring which is substituted in the para position.

12. The compound according to claim 2, wherein X is an aromatic heterocycle.

13. The compound according to claim 3, wherein X is an aromatic heterocycle.

14. A composition suitable for controlling harmful fungi, wherein said composition comprises a solid or liquid carrier and a compound according to claim 1.

15. A method for controlling phytopathogenic harmful fungi, comprising:
treating the fungi or the materials, plants, the soil or seeds to be protected against fungal attack with an effective amount of a compound according to claim 1.

16. A method for preparing a compound according to claim 1, comprising:

reacting pyridine derivatives of the formula II

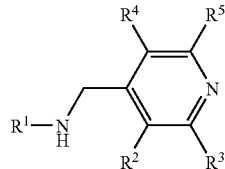

under basic conditions with a sulfonyl chloride of the formula III,

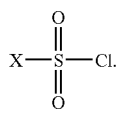

17. A method for preparing a compound according to claim 2, by comprising:

reacting pyridine derivatives of formula II

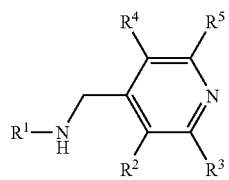

under basic conditions with a sulfonyl chloride of formula III

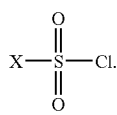

18. A method for preparing a compound according to claim 3, by comprising:

reacting pyridine derivatives of the formula II

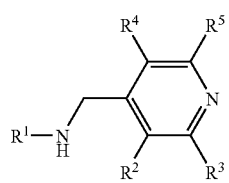

under basic conditions with a sulfonyl chloride of formula III

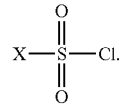

19. A method for preparing a compound according to claim 4, comprising:

reacting pyridine derivatives of the formula II

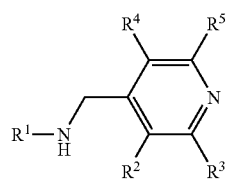

under basic conditions with a sulfonyl chloride of formula III

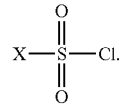

20. A method for preparing a compound according to claim 5, comprising:

reacting pyridine derivatives of formula II

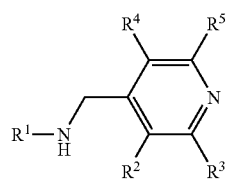

under basic conditions with a sulfonyl chloride of formula III

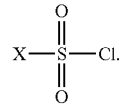

* * * * *